United States Patent
Dziubak et al.

(10) Patent No.: US 9,585,555 B2
(45) Date of Patent: Mar. 7, 2017

(54) OCT APPARATUS AND METHOD OF CONTROLLING THE SAME

(71) Applicant: CANON KABUSHIKI KAISHA, Tokyo (JP)

(72) Inventors: Tomasz Dziubak, Zawiercie (PL); Takashi Naba, Kawasaki (JP)

(73) Assignee: Canon Kabushiki Kaisha, Tokyo (JP)

(*) Notice: Subject to any disclaimer, the term of this patent is extended or adjusted under 35 U.S.C. 154(b) by 51 days.

(21) Appl. No.: 14/792,808

(22) Filed: Jul. 7, 2015

(65) Prior Publication Data

US 2016/0007847 A1 Jan. 14, 2016

(30) Foreign Application Priority Data

Jul. 14, 2014 (JP) ................. 2014-144567

(51) Int. Cl.
| | |
|---|---|
| *A61B 3/14* | (2006.01) |
| *A61B 3/10* | (2006.01) |
| *A61B 3/00* | (2006.01) |
| *A61B 3/12* | (2006.01) |
| *G01B 9/02* | (2006.01) |

(52) U.S. Cl.
CPC ............ *A61B 3/102* (2013.01); *A61B 3/0025* (2013.01); *A61B 3/1225* (2013.01); *A61B 3/14* (2013.01); *G01B 9/02064* (2013.01); *G01B 9/02091* (2013.01)

(58) Field of Classification Search
CPC ......... A61B 3/102; A61B 5/0066; A61B 3/12; A61B 3/14

USPC ......... 351/206, 246, 205, 200; 356/479, 497
See application file for complete search history.

(56) References Cited

U.S. PATENT DOCUMENTS

| | | | |
|---|---|---|---|
| 7,643,154 B2 | 1/2010 | Kikawa et al. | |
| 7,777,893 B2 | 8/2010 | Kikawa et al. | |
| 7,982,880 B2 | 7/2011 | Kikawa et al. | |
| 8,807,750 B2 | 8/2014 | Naba et al. | |
| 9,033,498 B2 | 5/2015 | Naba | |
| 2008/0151256 A1 | 6/2008 | Kikawa et al. | |
| 2008/0151260 A1 | 6/2008 | Kikawa et al. | |
| 2010/0188502 A1 | 7/2010 | Kikawa et al. | |
| 2013/0182220 A1 | 7/2013 | Naba | |
| 2014/0211155 A1* | 7/2014 | Sakagawa ............. A61B 3/113 351/206 |

FOREIGN PATENT DOCUMENTS

| | | |
|---|---|---|
| JP | 2008-154939 A | 7/2008 |
| JP | 2008-154941 A | 7/2008 |

* cited by examiner

*Primary Examiner* — Hung Dang
(74) *Attorney, Agent, or Firm* — Fitzpatrick, Cella, Harper & Scinto (57) ABSTRACT

In an OCT apparatus for obtaining a tomogram using optical interference between signal light and reference light, a first distance between a specific image and a coherence gate is obtained from a first tomogram obtained by imaging. The coherence gate is moved by a set moving distance along a predetermined moving direction. The positional relationship between the specific image and the coherence gate is determined based on the position of the specific image in a second tomogram obtained by imaging after movement of the coherence gate and the position of the specific image in the first tomogram.

20 Claims, 5 Drawing Sheets

OCT APPARATUS AND METHOD OF CONTROLLING THE SAME

BACKGROUND OF THE INVENTION

Field of the Invention

The present invention relates to an OCT apparatus for obtaining a tomogram by optical interference and a method of controlling the same.

Description of the Related Art

Various apparatuses are used at present as ophthalmic apparatuses using optical apparatuses. For example, various apparatuses such as a camera for anterior ocular segment, a fundus camera, and an SLO (Scanning Laser Ophthalmoscope) are used as optical apparatuses for observing an eye. In particular, an OCT (Optical Coherence Tomography) apparatus (to be referred to as an OCT apparatus hereinafter) is an apparatus for obtaining a tomogram of a sample at a high resolution, and is becoming indispensable as an ophthalmic apparatus in a specialty outpatient clinic for retina.

The OCT apparatus divides low-coherence light into reference light and observation light, irradiates a sample with the observation light, and uses interference between the reference light and reflected light from the sample, thereby forming an image in the observation light direction. The OCT apparatus scans the low-coherence light on the sample, thereby obtaining a tomogram of a section at a high resolution along the scan direction. For example, the OCT apparatus can capture a tomogram of the retina on the fundus of an eye to be inspected at a high resolution, and is widely used in ophthalmic diagnosis of retina and the like.

As a retinal tomogram obtained by the OCT apparatus, a scan called B scan is generally used. In the B scan, a scan in the retinal depth direction (Z direction) called A scan is performed a plurality of times while moving in the X direction, thereby obtaining a tomogram. The B scan allows a user to observe the internal state of the retina, as compared to an image of a conventional fundus camera or the like. It is therefore possible to obtain an image effective for observing a lesion in the retina such as macular degeneration or a macular hole in particular.

In imaging by the OCT apparatus, there exists a coherence gate that is a position where the reference light path and the observation light path have the same length. Japanese Patent Laid-Open Nos. 2008-154939 and 2008-154941 disclose a technique of adjusting an image position or signal-to-noise ratio (SN ratio) in an OCT image by adjusting the coherence gate position.

An OCT image has the origin at the coherence gate position and forms a tomogram by obtaining the values of the distance and reflection intensity. Hence, for example, when a retinal tomogram in a case where the coherence gate is located on the vitreous side with respect to the retina is defined as a normal image, a tomogram obtained in a case where the coherence gate is located on the choroid side with respect to the retina is a reverse image.

In addition, the reflection intensity (interference light intensity) of an image is the highest at the coherence gate position and lowers as the distance increases (called roll-off). For this reason, to obtain information of a retinal surface such as a nerve fiber layer concerning glaucoma, an OCT image is preferably obtained by placing the coherence gate on the upper retinal surface (vitreous side). On the other hand, to obtain information near a pigment epithelium layer concerning age-rated macular degeneration or the like, an OCT image is preferably obtained by placing the coherence gate on the lower retinal surface (choroid side). As described above, it is important in OCT imaging to determine whether the coherence gate is located on the vitreous side or choroid side with respect to the retina.

SUMMARY OF THE INVENTION

The present invention has been made in consideration of the above-described problem, and embodiments of the present invention provides an OCT apparatus capable of automatically determining the relationship between the position of a coherence gate and the position of a specific image in OCT imaging, and a method of controlling the same.

According to one aspect of the present invention, there is provided an OCT apparatus for obtaining a tomogram using optical interference between signal light and reference light, comprising: an obtaining unit configured to obtain a position of a specific image with respect to a coherence gate from a first tomogram obtained by imaging; a moving unit configured to move the coherence gate by a set moving distance along a predetermined moving direction; and a determination unit configured to determine a positional relationship between the specific image and the coherence gate based on the position of the specific image with respect to the coherence gate obtained from a second tomogram obtained by imaging after movement of the coherence gate and the position obtained by the obtaining unit.

According to another aspect of the present invention, there is provided a method of controlling an OCT apparatus for obtaining a tomogram using optical interference between signal light and reference light, comprising: an obtaining step of obtaining a position of a specific image with respect to a coherence gate from a first tomogram obtained by imaging; a moving step of moving the coherence gate by a set moving distance along a predetermined moving direction; and a determination step of determining a positional relationship between the specific image and the coherence gate based on the position of the specific image with respect to the coherence gate obtained from a second tomogram obtained by imaging after movement of the coherence gate and the position obtained in the obtaining step.

Further features of the present invention will become apparent from the following description of exemplary embodiments with reference to the attached drawings.

DESCRIPTION OF THE EMBODIMENTS

Figure 1:
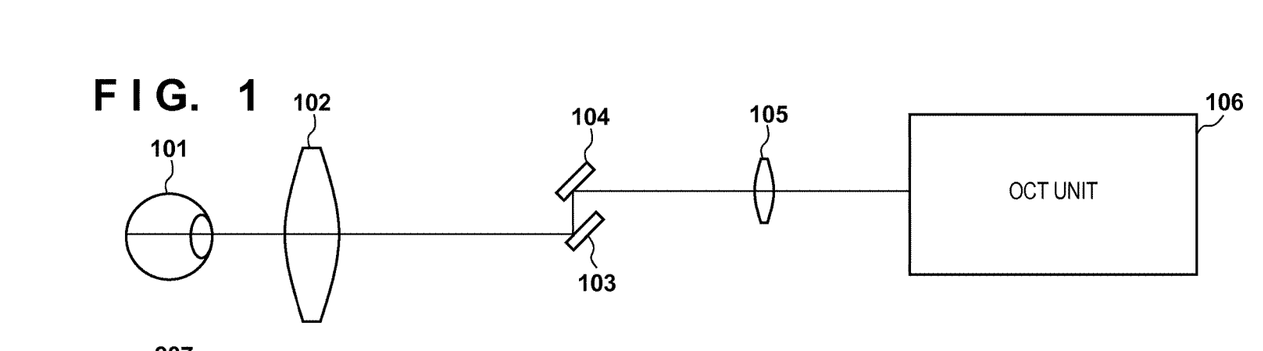
FIG. 1 is a block diagram showing an example of the arrangement of an OCT apparatus according to an embodiment.
Figure 2:
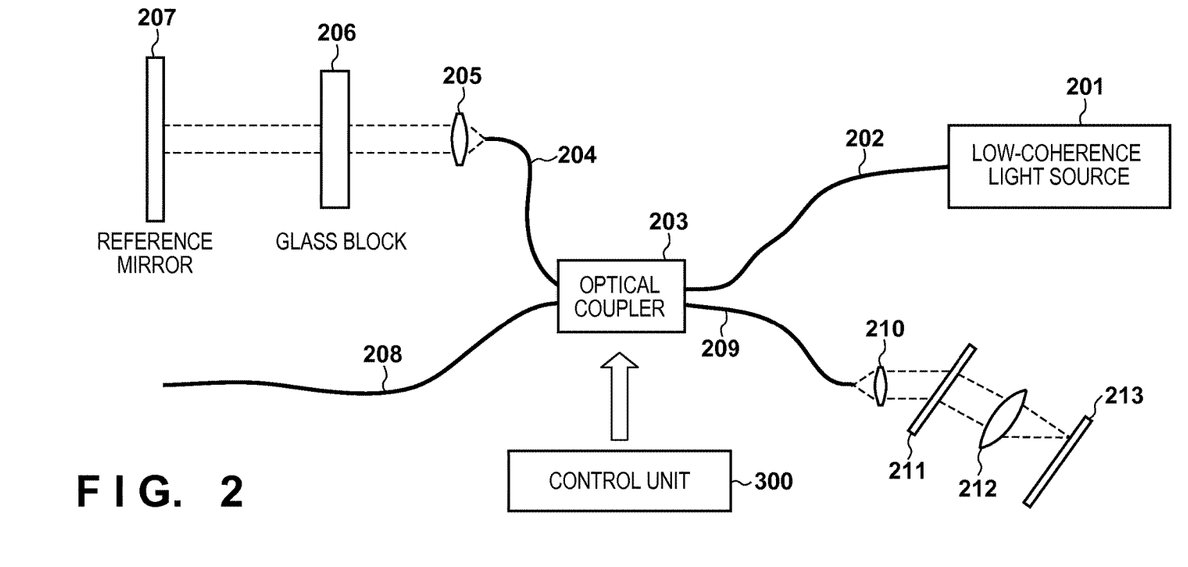
FIG. 2 is a block diagram showing an example of the arrangement of an OCT unit.
Figure 3:
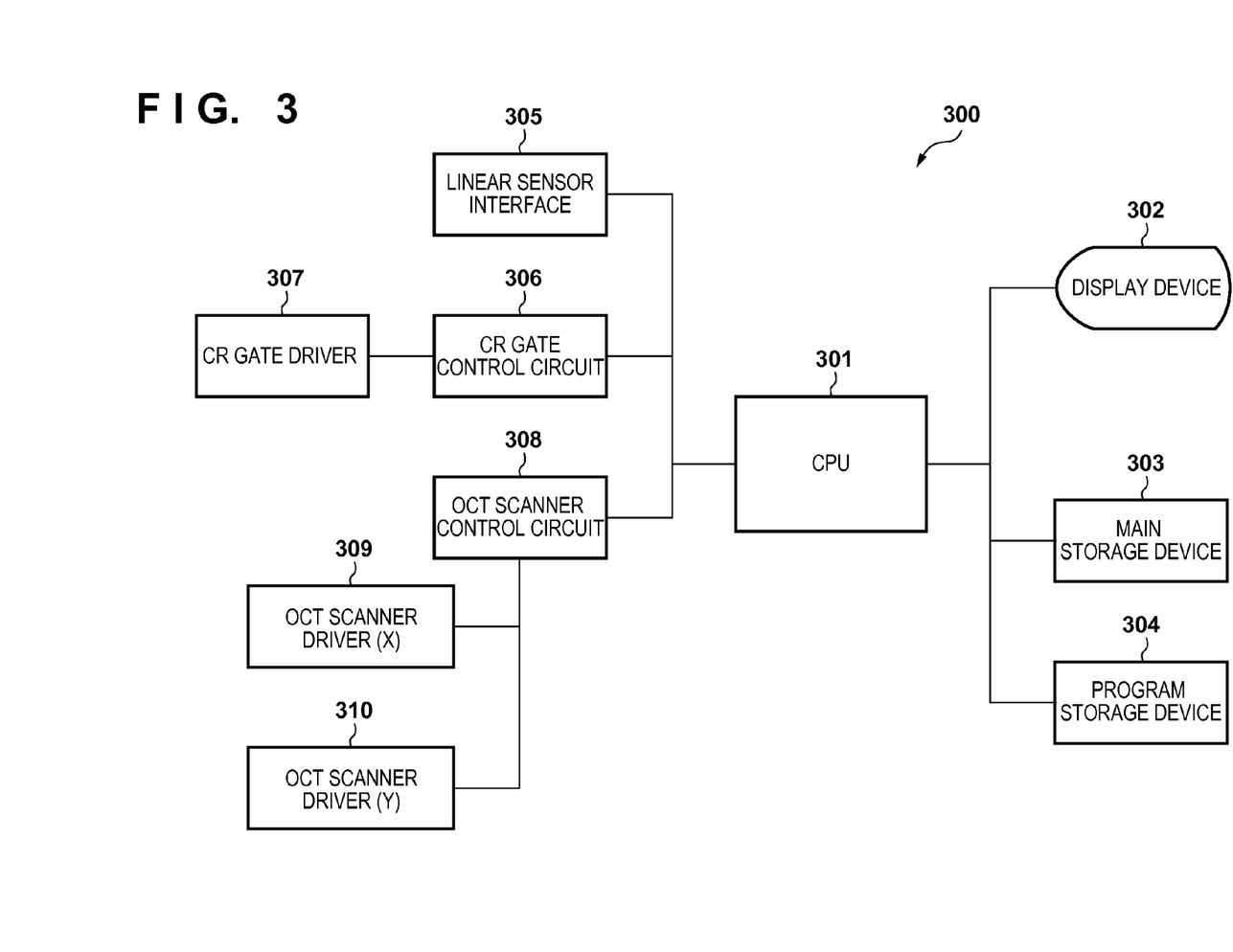
FIG. 3 is a block diagram showing an example of the arrangement of a control unit.
Figure 6:
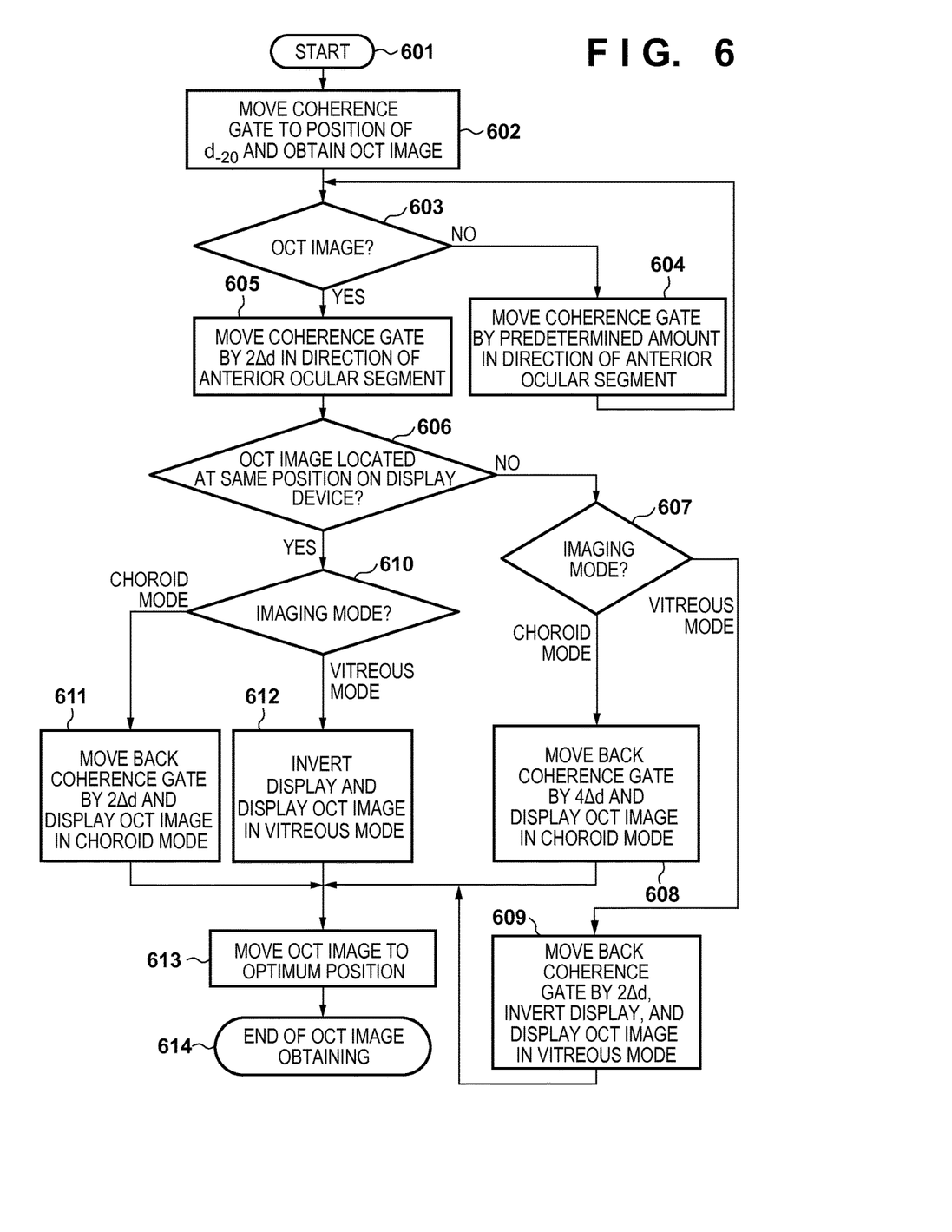
FIG. 6 is a flowchart showing an OCT imaging operation according to the embodiment.

A preferred embodiment of the present invention will now be described with reference to the accompanying drawings. In this embodiment, an optical coherence tomography apparatus (to be referred to as an OCT apparatus hereinafter) for obtaining a tomogram using optical interference between signal light and reference light will be exemplified. FIG. 1 is a block diagram of the OCT apparatus according to this embodiment. FIG. 2 is a block diagram of an OCT unit. FIG. 3 is a block diagram of a control unit. FIG. 6 is a flowchart executed by the control unit. The embodiment of the present invention will be described below with reference to these drawings.

<OCT Scan and Eye Piece Unit>

The scan mechanism of OCT will be described with reference to FIG. 1. Observation light (to be referred to as signal light hereinafter) from an OCT unit 106 is shaped into a parallel beam by a collimator lens 105, passes through an OCT-X scanner 104, an OCT-Y scanner 103, and an eye piece lens (or objective lens) 102, and enters an eye 101 to be inspected. The beam that has entered the eye 101 is reflected and scattered by the fundus of the eye and returns to the OCT unit 106 via the same optical path. Note that the OCT-Y scanner 103 and the OCT-X scanner 104 form a mechanism configured to two-dimensionally scan the signal light. The above-described portion outside the OCT unit 106 is also called a sample arm.

<OCT Unit 106>

The arrangement of the OCT unit 106 will be described next with reference to FIG. 2. The OCT unit 106 divides low-coherence light into reference light and signal light and superimposes the signal light returned via the eye 101 on the reference light returned via a reference object, thereby generating interference light. In the OCT unit 106, a detection signal obtained by dispersing the interference light is input to a CPU 301 of a control unit 300. The CPU 301 analyzes the detection signal and forms a tomogram or 3D image of the fundus of the eye.

A low-coherence light source 201 is formed from a wide-band light source that outputs low-coherence light. In this embodiment, an SLD (Super Luminescent Diode) is used as the wide-band light source. The low-coherence light is light including light of a wavelength in the near infrared range and having a coherence length of several tens of micrometers. The low-coherence light has a wavelength within the range of, for example, about 800 nm to 900 nm.

Low-coherence light output from the low-coherence light source 201 is guided to an optical coupler 203 via an optical fiber 202. The optical fiber 202 is normally formed from a single mode fiber. The optical coupler 203 divides the low-coherence light into reference light and signal light.

The reference light obtained from the optical coupler 203 is guided by an optical fiber 204, shaped into a parallel beam by a collimator lens 205, passed through a glass block 206, and reflected by a reference mirror 207. The glass block 206 functions as a dispersion compensation that makes the dispersion characteristic of the reference light match that of the signal light. The reference light reflected by the reference mirror 207 passes through the same optical path and enters the optical fiber 204. The reference mirror 207 can move in the traveling direction of the reference light. This can resolve the shift of the distance (optical path length) between the reference light and the signal light caused by, for example, the axial length of the eye 101 or the distance between the eye piece lens 102 and the eye 101. The above-described optical path from the optical coupler 203 to the reference mirror 207 shown in FIG. 2 is also called a reference arm.

On the other hand, the signal light obtained from the optical coupler 203 is guided by an optical fiber 208 to irradiate the retina of the eye 101 via the OCT-X scanner 104, the OCT-Y scanner 103, and the eye piece lens 102 shown in FIG. 1. The signal light that has irradiated the retina is reflected and scattered by the retina and the like, and the reflected and scattered signal light is re-input to the optical fiber 208 and guided to the optical coupler 203. In the optical coupler 203, the signal light introduced from the optical fiber 208 is made to interfere with the reference light introduced from the optical fiber 204, thereby obtaining interference light. The interference light is passed through an optical fiber 209, shaped into a parallel beam by a collimator lens 210, and guided to a diffraction grating 211. The interference light is dispersed by the diffraction grating 211, and forms an image on a one-dimensional sensor 213 via a lens 212. As the one-dimensional sensor 213, a CCD sensor, a CMOS sensor, or the like is usable. A signal generated by dispersing the interference light is obtained from the one-dimensional sensor 213, and the obtained signal is input to the control unit 300.

<Control Unit 300>

The control unit 300 will be described next with reference to FIG. 3. The CPU 301 that is a central processing unit is connected to a display device 302, a main storage device 303 (formed from, for example, a RAM), a program storage device 304 (formed from, for example, a ROM). The CPU 301 is also connected to a linear sensor interface 305 that receives data from the one-dimensional sensor 213 as the output of the OCT, a coherence gate control circuit (to be referred to as a CR gate control circuit 306 hereinafter), and an OCT scanner control circuit 308.

The CR gate control circuit 306 adjusts the coherence gate position by a CR gate driver 307. That is, the CR gate control circuit 306 moves the coherence gate along a predetermined direction by the CR gate driver 307. In this embodiment, the predetermined direction is the traveling direction in the outgoing path or returning path of signal light. The direction of the outgoing path is the direction toward the choroid, and the direction of the returning path is the direction toward the anterior ocular segment. The OCT scanner control circuit 308 controls the OCT-X scanner 104 and the OCT-Y scanner 103 by an OCT scanner driver (X) 309 and an OCT scanner driver (Y) 310. For example, the OCT scanner control circuit 308 controls the x- and y-direction scan center positions, the x- and y-direction scan widths, and the scan rate based on an instruction from the CPU 301. The CPU 301 can know the scan position of signal light from the OCT scanner control circuit 308. The CPU 301 executes various kinds of control in the OCT apparatus by a program stored in the program storage device 304.

Figure 4A:
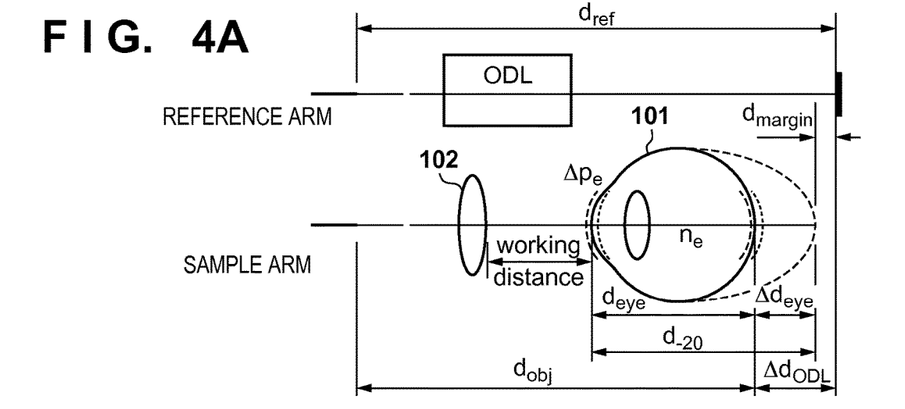
FIGS. 4A to 4D are views for explaining the position of an eye to be inspected and a coherence gate.

The positional relationship between the eye and the coherence gate in the OCT apparatus will be described next with reference to FIG. 4A. The coherence gate position is the position where the optical path length of reference light equals that of observation light, and can be adjusted by changing the optical path length of reference light. For example, in FIG. 2, the optical path length of reference light can be changed by moving the reference mirror 207. Note that the coherence gate position is adjusted using the above-described CR gate control circuit 306. FIG. 4A illustrates such a change in the optical path length of reference light as ODL (Optical Delay Line). Referring to FIG. 4A, $d_{ref}$ is the optical path length of reference light, $d_{obj}$ is the optical path length up to the retina of a normal eye, $d_{eye}$ is the distance from the corneal surface to the retina of an eye $d_{-20}$ is the distance from the corneal surface to the retina of a nearsighted eye of a degree of −20

$\Delta d_{eye}$ is the difference between $d_{eye}$ and $d_{-20}$, and $\Delta P_e$ is the individual difference of the distance from the lens to the eyeball To obtain a retinal image by the OCT apparatus, the coherence gate needs to be placed near the retina. Since it is generally assumed that nobody can have a nearsightedness of a degree of −20 or more, the coherence gate is moved close to the eye from a position spaced apart from the position of $d_{-20}$ by a margin $d_{margin}$ (the coherence gate is moved in the direction of the anterior ocular segment). A difference $\Delta d_{ODL}$ between the position of the coherence gate and the position of an average eye (normal eye) by ODL at this time is given by $$\Delta d_{ODL} = n_e \Delta d_{eye} + \Delta P_e + d_{margin}$$

where $n_e$ is the refractive index of the eye. By decreasing $\Delta d_{ODL}$, an OCT image of the retina can be found and observed.

Figure 4B:
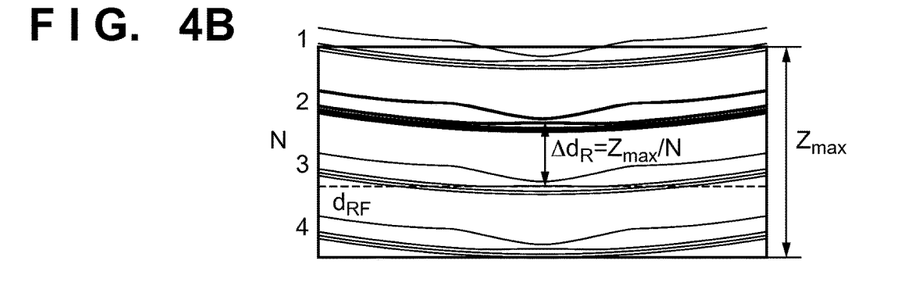

FIG. 4B shows a display example of an OCT tomogram. In this example, the coherence gate is moved from the choroid side to the anterior ocular segment side. The lower end of the tomogram display is located at the same position as the coherence gate, and the upper end is located at the same position as an obtaining depth $Z_{max}$ of the OCT image. In this example, the coherence gate is located on the choroid side with respect to the retina. This state is called a choroid mode. On the other hand, a state in which the coherence gate is located on the anterior ocular segment side (vitreous side) with respect to the retina is called a vitreous mode. Note that in the vitreous mode, a tomogram is displayed such that the upper end is located at the same position as the coherence gate, and the lower end is located at the same position as the obtaining depth $Z_{max}$ of the OCT image. FIG. 4B shows a change in the position of a retinal image when the coherence gate is moved in steps corresponding to ¼ of $Z_{max}$.

Figure 4C:
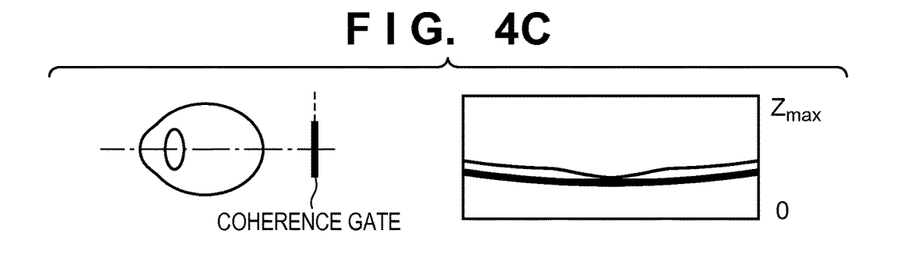
Figure 4D:
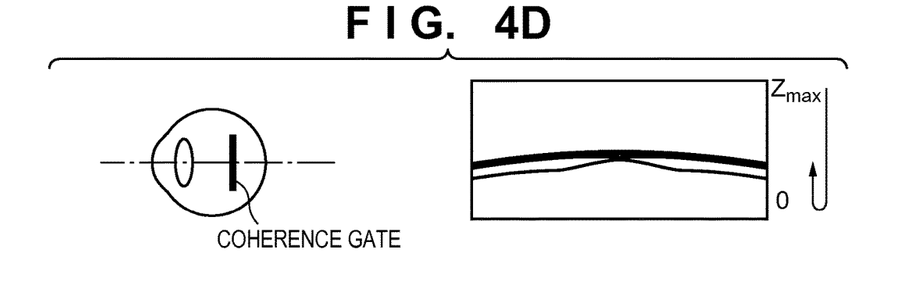

FIG. 4C shows a display example of a tomogram when the coherence gate is adjusted to an appropriate position. However, if the coherence gate moving amount per step is increased to shorten time, the coherence gate may overshoot the retina. FIG. 4D shows the coherence gate and an OCT image in this case. In FIGS. 4C and 4D, the mode changed from the choroid mode to the vitreous mode as the coherence gate moves. However, since the display mode does not correspond to the vitreous mode, the retinal image is inverted in FIG. 4D. Hence, when the coherence gate moving amount per step is increased, it is necessary to determine the positional relationship between the coherence gate and the retina, that is, whether the coherence gate is located before or after the retina.

Figure 5A:
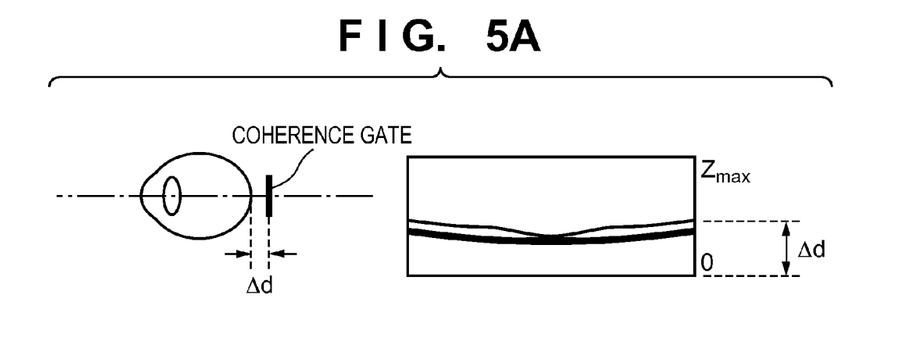
FIGS. 5A to 5C are views for explaining a method of determining the positional relationship between a retina and a coherence gate.
Figure 5B:
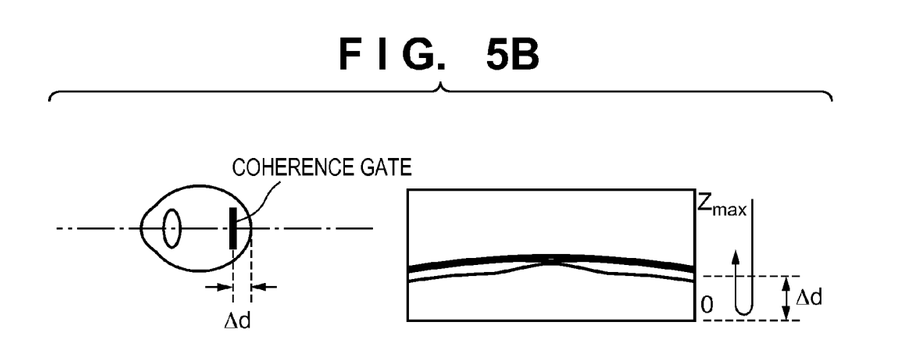
Figure 5C:
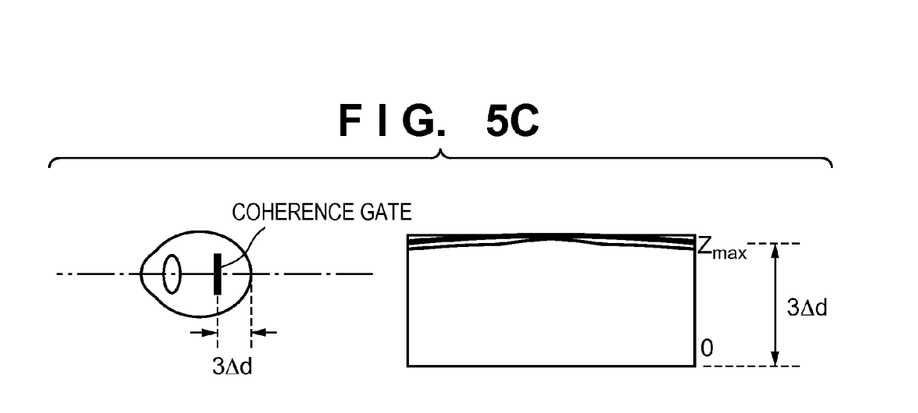

A method of determining the positional relationship between the coherence gate and the retina as a specific OCT image will be described with reference to FIGS. 5A to 5C. Assume that the distance between the coherence gate and the retina is obtained as Δd from a tomogram obtained at the coherence gate position in the choroid mode in which the retina exists before the coherence gate (on the anterior ocular segment side) as shown in FIG. 5A. When the coherence gate is moved by 2Δd in the direction of the anterior ocular segment, the moved coherence gate is located at a position in the vitreous mode. The distance between the coherence gate and the retina is still Δd. Hence, a tomogram as shown in FIG. 5B is obtained. However, since the coherence gate position changes from the choroid mode to the vitreous mode, the OCT image of the retina is inverted.

In a case where the OCT image of the retina appears behind the coherence gate, as shown in FIG. 5B (coherence gate position in the vitreous mode), if the coherence gate is moved by 2Δd in the direction of the anterior ocular segment, the distance between the coherence gate and the retina changes to 3Δd. As a result, the OCT image of the retina appears at a position totally different from that in FIG. 5B or outside the display area of the display device, as shown in FIG. 5C. In this case, if the coherence gate is moved by 2Δd from the position shown in FIG. 5B in the direction opposite to the anterior ocular segment, the state shown in FIG. 5A is obtained, and an OCT image in the choroid mode is obtained.

When a tomogram including an OCT image is obtained as described above, the coherence gate is moved by 2Δd in the direction of the anterior ocular segment to determine whether the coherence gate is located on the choroid side (choroid mode) or on the vitreous side (vitreous mode). That is, when the coherence gate is moved by 2Δd in the direction of the anterior ocular segment, it is determined whether a specific OCT image (retinal image) is obtained at the same position in tomograms before and after the movement, thereby determining the coherence gate position.

The above-described adjustment of the coherence gate position will be explained with reference to the flowchart of FIG. 6. When OCT image obtaining starts in step 601, the CPU 301 moves the coherence gate to a position spaced apart from a position corresponding to $d_{-20}$ by the margin $d_{margin}$ as the initial position of the coherence gate in step 602. The CPU 301 obtains a tomogram by OCT at this coherence gate position. Next, the CPU 301 determines whether a specific OCT image exists in the obtained tomogram (step 603). If the OCT image does not exist, the coherence gate is moved by a predetermined distance in the direction of the anterior ocular segment (step 604), and a tomogram is obtained again. In this embodiment, it is determined whether a retinal image is obtained as the specific OCT image. Note that detection of a retinal image from an OCT tomogram can be implemented using a known technique.

On the other hand, upon determining in step 603 that the OCT image is obtained, the CPU 301 obtains the distance between the specific OCT image and the coherence gate from the tomogram, and sets the moving distance of the coherence gate based on the distance. In this embodiment, the CPU 301 sets the moving distance of the coherence gate twice as much as the distance obtained from the tomogram, that is, 2Δd, and moves the coherence gate by 2Δd in the direction of the anterior ocular segment (step 605).

Next, the CPU 301 compares the position of the specific OCT image in the tomogram before the movement of the coherence gate in step 605 and that after the movement, and determines, based on the comparison result, the positional relationship between the specific OCT image and the coherence gate along the direction of signal light. In this embodiment, the CPU 301 determines whether the specific OCT image in the tomogram after the movement of the coherence gate in step 605 exists at the same position as detected in step 603 (step 606). Note that the positions need not strictly be the same, and it is determined whether a change in the position of the OCT image between the OCT tomograms obtained before and after the movement of the coherence gate falls within a predetermined range.

In this processing, the coherence gate is moved toward the anterior ocular segment. Hence, if it is determined in step 606 that the OCT image does not exist at the same position, the tomogram in which the OCT image is detected in step 603 is determined to have been captured in the vitreous mode. Then, processing from step 607 is performed. First, the CPU 301 determines whether the imaging mode designated by the user via a user interface (not shown) is the choroid mode or the vitreous mode (step 607). If the imaging mode designated by the user is the choroid mode, the CPU 301 moves back the coherence gate by 4Δd and displays the OCT image (step 608). With this processing, a tomogram in the choroid mode in which the distance between the retina and the coherence gate is set to Δd is obtained. If the imaging mode designated by the user is the vitreous mode, the CPU 301 moves back the coherence gate by 2Δd, inverts the display, and displays the OCT image (step 609). With this processing, a tomogram in the vitreous mode in which the distance between the retina and the coherence gate is set to Δd is obtained.

On the other hand, if it is determined in step 606 that the OCT image exists at the same position, the CPU 301 determines that the tomogram in which the OCT image is detected in step 603 has been captured in the choroid mode, and performs processing from step 610. First, the CPU 301 determines whether the imaging mode designated by the user is the choroid mode or the vitreous mode (step 610). If the imaging mode designated by the user is the choroid mode, the CPU 301 moves back the coherence gate by 2Δd and displays the OCT image (step 611). With this processing, a tomogram in the choroid mode in which the distance between the retina and the coherence gate is set to Δd is obtained. If the imaging mode designated by the user is the vitreous mode, the CPU 301 inverts the display and displays the OCT image without moving the coherence gate (step 612). With this processing, a tomogram in the vitreous mode in which the distance between the retina and the coherence gate is set to Δd is obtained.

In step 613, the CPU 301 finely adjusts the coherence gate position such that the OCT image (retinal image) is located at an appropriate position in the image. Obtaining of the OCT image thus ends (step 614).

Note that in the above example, the coherence gate is moved from the choroid toward the anterior ocular segment to search for an OCT image. However, the same control as described above can also be performed even when the coherence gate is moved from the choroid to the anterior ocular segment. In this case, the choroid mode and the vitreous mode are replaced with each other.

In the above embodiment, an example has been described in which a retinal image is used as a specific OCT image, and the choroid mode and the vitreous mode are determined based on the positional relationship between the retina and the coherence gate. However, the specific OCT image is not limited to the retina. In short, the coherence gate is moved based on the first distance between the specific OCT image and the coherence gate. Then, the distance between the specific OCT image and the coherence gate in a tomogram obtained after movement is compared with the first distance, thereby obtaining the positional relationship between the coherence gate and the specific OCT image in the traveling direction in the outgoing path of signal light.

With the processing of steps 605 and 606, the positional relationship between the coherence gate and the specific OCT image can be obtained. From the positional relationship, the CPU 301 can determine one of the first mode in which the coherence gate is arranged before the specific OCT image in the traveling direction in the outgoing path of signal light and the second mode in which the coherence gate is arranged behind. Based on this determination, the coherence gate is moved by an integer multiple such as two times or four times of the distance. This makes the display adaptable to the mode (first mode or second mode) designated by the user.

Note that although it is also possible to gradually move the coherence gate from the choroid side and sequentially determine the presence/absence of a tomogram so as to determine the mode as the choroid mode when a tomogram has appeared, the time to move the coherence gate increases. On the other hand, according to this embodiment, since the positional relationship between a tomogram and the coherence gate is used, as described above, whether the mode is the choroid mode or the vitreous mode can be determined by determining the presence/absence of a tomogram every time the coherence gate is moved from the choroid side at a predetermined interval. That is, according to this embodiment, it is possible to quickly determine whether the mode is the choroid mode or the vitreous mode.

If the purpose is to determine the position of the coherence gate with respect to the specific OCT image, the moving amount of the coherence gate in step 605 need not be 2Δd. For example, a moving distance shorter than 2Δd may be set, and it may be determined whether the distance between the specific OCT image and the coherence gate has shortened before and after the movement of the coherence gate.

Note that in the above embodiment, after the first tomogram is obtained, the coherence gate is moved by 2Δd, and the second tomogram is then obtained. However, the present invention is not limited to this. For example, to simply determine the positional relationship between the coherence gate and a specific image (retinal image), the coherence gate may be moved by a predetermined distance independently of the measured distance Δd. In this case, for example, after the distance Δd between the coherence gate and the retinal tomogram is obtained from the first tomogram, the coherence gate is moved by a predetermined distance, and the second tomogram is then obtained. By measuring a change in the positional relationship (a change in the distance) between the coherence gate and the specific OCT image (retinal tomogram) in the first tomogram and the second tomogram, the positional relationship between the coherence gate and the specific OCT image can be obtained. For example, when the coherence gate is moved to the anterior ocular segment side by a distance x from the state shown in FIG. 5A, the distance Δd between the retina and the coherence gate after the movement becomes shorter than the distance x. It is therefore found that the state shown in FIG. 5A is the choroid mode. In addition, when the coherence gate is moved to the anterior ocular segment side by the distance x from the state shown in FIG. 5B, the distance Δd between the retina and the coherence gate after the movement becomes longer than the distance x. It is therefore found that the state shown in FIG. 5B is the vitreous mode.

As described above, according to the above embodiment it is possible to automatically determine the relationship between the position of the coherence gate and the position of a specific image in OCT imaging.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-144567, filed Jul. 14, 2014 which is hereby incorporated by reference herein in its entirety.

What is claimed is:

1. An OCT apparatus for obtaining a tomogram using optical interference between signal light and reference light, comprising:
    an obtaining unit configured to obtain a position of a specific image with respect to a coherence gate from a first tomogram obtained by imaging;
    a moving unit configured to move the coherence gate by a set moving distance along a predetermined moving direction; and
    a determination unit configured to determine a positional relationship between the specific image and the coherence gate based on the position of the specific image with respect to the coherence gate obtained from a second tomogram obtained by imaging after movement of the coherence gate and the position obtained by said obtaining unit.

2. The apparatus according to claim 1, wherein said obtaining unit obtains, from the first tomogram, a first distance from the coherence gate to the specific image, and
    said determination unit determines the positional relationship based on the first distance and a second distance from the coherence gate to the specific image, which is obtained from the second tomogram.

3. The apparatus according to claim 2, wherein said moving unit sets the moving distance based on the first distance.

4. The apparatus according to claim 3, wherein the moving distance is twice as much as the first distance, and
    said determination unit determines the positional relationship based on whether a change in the position of the specific image between the first tomogram and the second tomogram falls within a predetermined range.

5. The apparatus according to claim 4, wherein said determination unit determines, based on the positional relationship, which one of a first mode in which the coherence gate is arranged before the specific image concerning a traveling direction in an outgoing path of the signal light and a second mode in which the coherence gate is arranged behind the specific image is a mode in which one of the first tomogram and the second tomogram is captured.

6. The apparatus according to claim 5, wherein the specific image is a retina, and
    said determination unit determines whether the coherence gate is located on a vitreous side or choroid side with respect to the retina in one of the first tomogram and the second tomogram.

7. The apparatus according to claim 4, wherein the specific image is a retina, and
    said determination unit determines whether the coherence gate is located on a vitreous side or choroid side with respect to the retina in one of the first tomogram and the second tomogram.

8. The apparatus according to claim 3, wherein said determination unit determines, based on the positional relationship, which one of a first mode in which the coherence gate is arranged before the specific image concerning a traveling direction in an outgoing path of the signal light and a second mode in which the coherence gate is arranged behind the specific image is a mode in which one of the first tomogram and the second tomogram is captured.

9. The apparatus according to claim 8, wherein the specific image is a retina, and
    said determination unit determines whether the coherence gate is located on a vitreous side or choroid side with respect to the retina in one of the first tomogram and the second tomogram.

10. The apparatus according to claim 3, wherein the specific image is a retina, and
    said determination unit determines whether the coherence gate is located on a vitreous side or choroid side with respect to the retina in one of the first tomogram and the second tomogram.

11. The apparatus according to claim 2, wherein said determination unit determines, based on the positional relationship, which one of a first mode in which the coherence gate is arranged before the specific image concerning a traveling direction in an outgoing path of the signal light and a second mode in which the coherence gate is arranged behind the specific image is a mode in which one of the first tomogram and the second tomogram is captured.

12. The apparatus according to claim 11, further comprising:
    a designation unit configured to designate one of the first mode and the second mode; and
    a unit configured to move the coherence gate to one of a position at which the first tomogram is captured and a position moved from the position by an integer multiple of the first distance based on the positional relationship determined by said determination unit so as to make the positional relationship between the coherence gate and the specific image correspond to the mode designated by said designation unit.

13. The apparatus according to claim 12, wherein the specific image is a retina, and
    said determination unit determines whether the coherence gate is located on a vitreous side or choroid side with respect to the retina in one of the first tomogram and the second tomogram.

14. The apparatus according to claim 11, wherein the specific image is a retina, and
    said determination unit determines whether the coherence gate is located on a vitreous side or choroid side with respect to the retina in one of the first tomogram and the second tomogram.

15. The apparatus according to claim 2, wherein the specific image is a retina, and
said determination unit determines whether the coherence gate is located on a vitreous side or choroid side with respect to the retina in one of the first tomogram and the second tomogram.

16. The apparatus according to claim 1, wherein said moving unit moves the coherence gate by changing an optical path length of the reference light.

17. The apparatus according to claim 16, wherein the specific image is a retina, and
said determination unit determines whether the coherence gate is located on a vitreous side or choroid side with respect to the retina in one of the first tomogram and the second tomogram.

18. The apparatus according to claim 1, wherein the specific image is a retina, and
said determination unit determines whether the coherence gate is located on a vitreous side or choroid side with respect to the retina in one of the first tomogram and the second tomogram.

19. A method of controlling an OCT apparatus for obtaining a tomogram using optical interference between signal light and reference light, comprising:
an obtaining step of obtaining a position of a specific image with respect to a coherence gate from a first tomogram obtained by imaging;
a moving step of moving the coherence gate by a set moving distance along a predetermined moving direction; and
a determination step of determining a positional relationship between the specific image and the coherence gate based on the position of the specific image with respect to the coherence gate obtained from a second tomogram obtained by imaging after movement of the coherence gate and the position obtained in the obtaining step.

20. A non-transitory computer-readable storage medium storing a program configured to cause a computer to execute a method of controlling an OCT apparatus for obtaining a tomogram using optical interference between signal light and reference light, comprising:
an obtaining step of obtaining a position of a specific image with respect to a coherence gate from a first tomogram obtained by imaging;
a moving step of moving the coherence gate by a set moving distance along a predetermined moving direction; and
a determination step of determining a positional relationship between the specific image and the coherence gate based on the position of the specific image with respect to the coherence gate obtained from a second tomogram obtained by imaging after movement of the coherence gate and the position obtained in the obtaining step.

* * * * *